United States Patent [19]

Jaeschke et al.

[11] 4,332,322

[45] Jun. 1, 1982

[54] FOLDER TO HOLD COIL OF PLASTIC TUBING WITH CLAMP AND FITTINGS

[75] Inventors: Harold R. Jaeschke, Milwaukee; Alan Linder, Wauwatosa; Daniel J. Boyle, Hartland, all of Wis.

[73] Assignee: Champion International Corporation, Stamford, Conn.

[21] Appl. No.: 182,854

[22] Filed: Sep. 2, 1980

[51] Int. Cl.³ .......................... B65D 83/10; B65D 5/50
[52] U.S. Cl. ..................................... 206/364; 206/485; 206/491; 206/363
[58] Field of Search ............... 206/303, 363, 364, 477, 206/485, 476, 482, 491, 495

[56] References Cited

U.S. PATENT DOCUMENTS

| | | | |
|---|---|---|---|
| 2,101,355 | 12/1937 | Wonder | 206/303 X |
| 2,969,146 | 1/1961 | Metz | 206/364 |
| 4,023,678 | 5/1977 | Fiedler | 206/485 X |
| 4,049,120 | 9/1977 | Bower | 206/491 X |
| 4,134,493 | 1/1979 | Cech | 206/485 X |

Primary Examiner—Steven M. Pollard
Attorney, Agent, or Firm—Evelyn M. Sommer

[57] ABSTRACT

A folder-container for a sterile tube and fittings. The folder-container positioning the tube and fittings in a single package which may be wrapped with sheet material such as a thermoplastic sealable material. The folder-container bottom wall is die-cut to provide a plurality of upstanding tabs to receive the coiled tube and any tubular fitting attached thereto and is arranged to position any other fitting associated with said tube.

4 Claims, 4 Drawing Figures

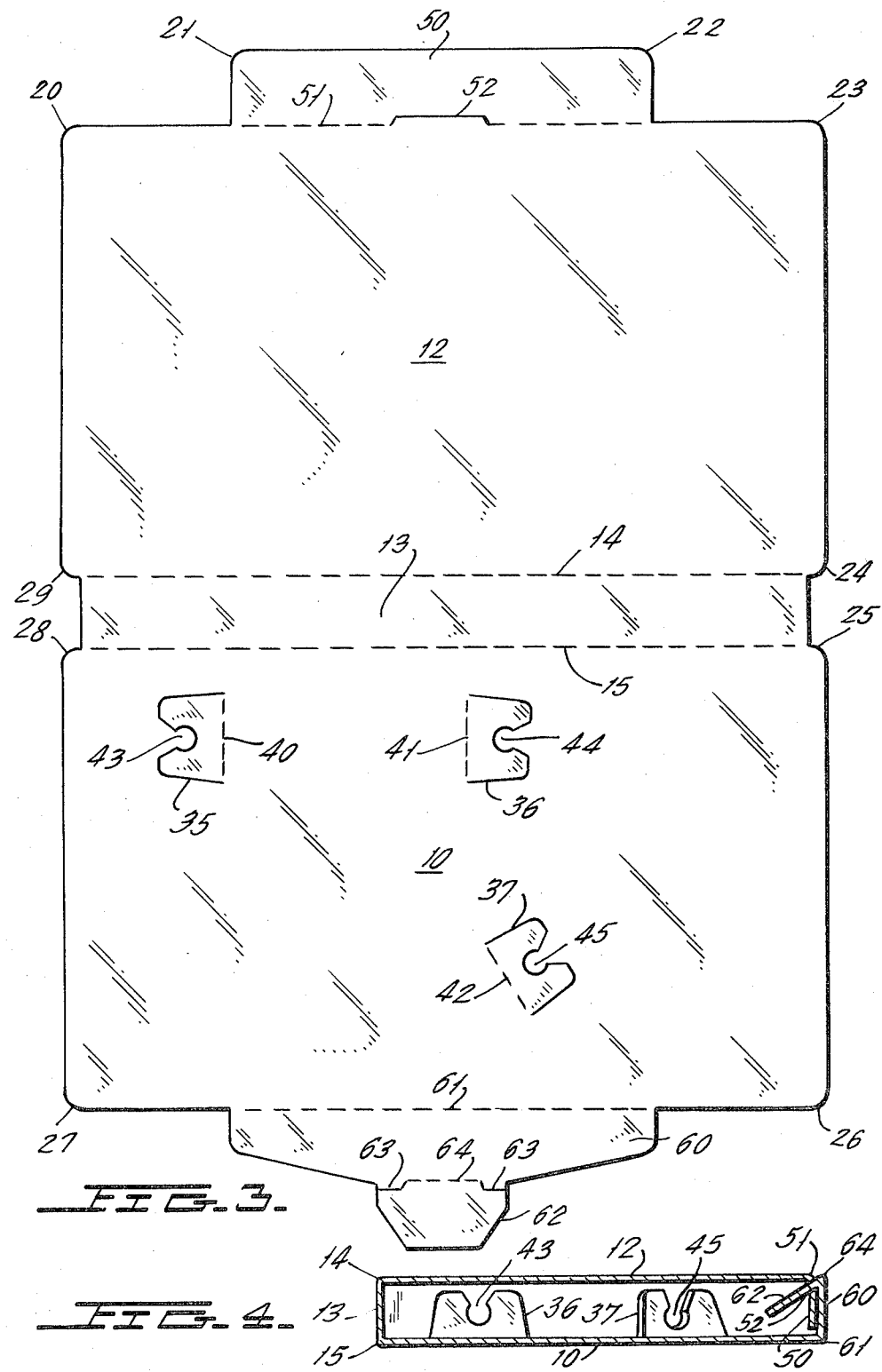

FOLDER TO HOLD COIL OF PLASTIC TUBING WITH CLAMP AND FITTINGS

The present invention relates to containers and more particularly to a die cut folder for securing a coil of plastic tubing with a large metal clamp and connector fittings.

In the construction and formation of containers or packages for plastic tubing with fittings of various kinds such as structures utilized in connection with medical work there are two major factors involved:

One is the packaging of the material so that it will withstand the rigors of storage and shipment and nevertheless be readily available when needed. Second is the packaging of the material so that it will remain clean and, where required, sterile from the point of manufacture and packaging up to the point of actual use.

In particular where the tubing is supplied with appropriate fittings the packaging of the material so that the fittings will not be damaged and will be held securely and so that the tubing will not itself be subject to unnecessary abrasion during shipment becomes most important.

Heretofor complex packages have been devised sometimes consisting of sets of packages where one package will carry one or more of the fittings, the other package the tubing and the third package additional fittings, all of them bound together so that they can be shipped as a single unit.

In other instances where attempts have been made to package the material by so-called vacuum packaging, the problems encountered in opening the package at the time when treatment is to occur or under sterile conditions may become difficult owing to the manner of packaging itself.

The primary object of the present invention is the provision of a container for tubing and fittings so that the tubing and fittings will be held rigidly in place, while at the same time the container may be readily folded or closed around the tubing and fittings and inserted in a package which may be sterilized. The structure itself is so arranged that it may readily be opened and readily be used under operating room or other conditions where a sterile environment is necessary without the necessity for additional implements for opening the package and without the need for excessive manipulation.

Essentially the present invention comprises a die cut folder which may readily be folded up around the tubing and its fittings and provides inherently, by bent up tabs, positioning devices for positioning both the tubing and the fittings so that they will be securely positioned within the container; the said folder or container also providing integrally therewith interlocking elements which will close the container; the container also being arranged so that it may then be placed in a film-type dust and microbe excluding container which may be sealed around it.

In addition to the foregoing, while the dust excluding covering for the container may constitute a thermoplastic material which has sufficient tensile strength to resist the tearing thereof; such material may not have suffificient strength to resist abrasion owing to sharp points or sharp boundaries and may thus be torn. Since the material forming the outer covering for the container is wrapped closely about the container, sharp corners on the container are replaced by curved areas so that no sharp point will be provided to initiate a tear in the wrapping structure.

The foregoing and many other objects of the present invention will become obvious in the following description and drawings in which:

FIG. 3 is a plan view of the blank from which the container of FIGS. 1 and 2 is formed.

FIG. 4 is a cross-sectional view taken from line 4—4 of FIG. 2 looking in the direction of the arrows.

Figure 1:
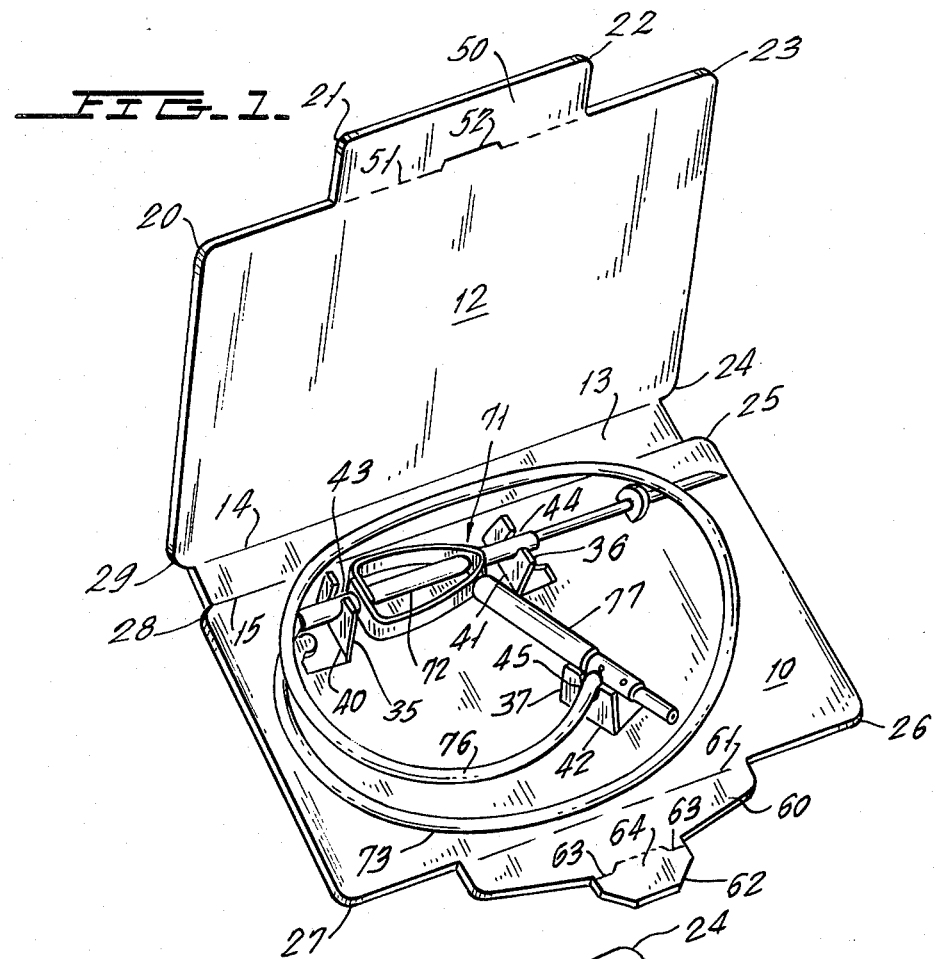
FIG. 1 is a view in perspective of the folder-container of the present invention with one form of plastic tubing and two types of fittings mounted thereon,—one fitting at each end of the tubing. It may be understood that under appropriate circumstances, one or both ends of the tube may be free of fittings and nevertheless will be supported in the same way.

Referring to the drawings, the novel folder container of the present invention is provided with a bottom wall 10 and a top wall or cover 12 connected to the bottom wall by the panel 13. Panel 13 is hingedly connected along the fold line 14 to the top wall 12 and along the fold line 15 to the bottom wall 10.

It will be noted that all of the corners of the blank which might engage an outer wrapper which may be wrapped around the container after it is erected in the manner hereinafter described are rounded off as seen at the various corners 20, 21, 22, 23, 24, 25, 26, 27, 28, 29.

It should also be noted that the corners 24 of the cover 12 and 25 of the bottom wall 10, as well as the corners 29 of the cover 12, and 28 of the bottom wall 10 extend beyond the panel 13 so that the panel 13 is recessed and only the curved corners are available at the margins of the container.

The bottom wall 10 of the blank is also provided with die cut tabs 35, 36, 37 which are cut on three sides and connected by the respective bend lines 40, 41, 42 to the bottom wall so that they may be folded to an upstanding or erect position substantially normal to the bottom wall 10 as seen in FIGS. 1 and 4.

The tabs 35, 36, 37 are formed with the notched recesses 43, 44, 45 to receive and frictionally retain a plastic or other tube. In other words, the recesses 43, 44, 45 and the notches extending thereinto are so shaped that owing to the flexibility of the carton material the tube may be forced therein, slightly deforming the material of the tabs 35, 36, 37 and thereby be held securely.

The top wall 12 is provided with the extension 50 connected thereto by the fold line 51 and having the notched portion 52 providing a slot which will receive the locking tab 62 hereinafter described.

Figure 2:
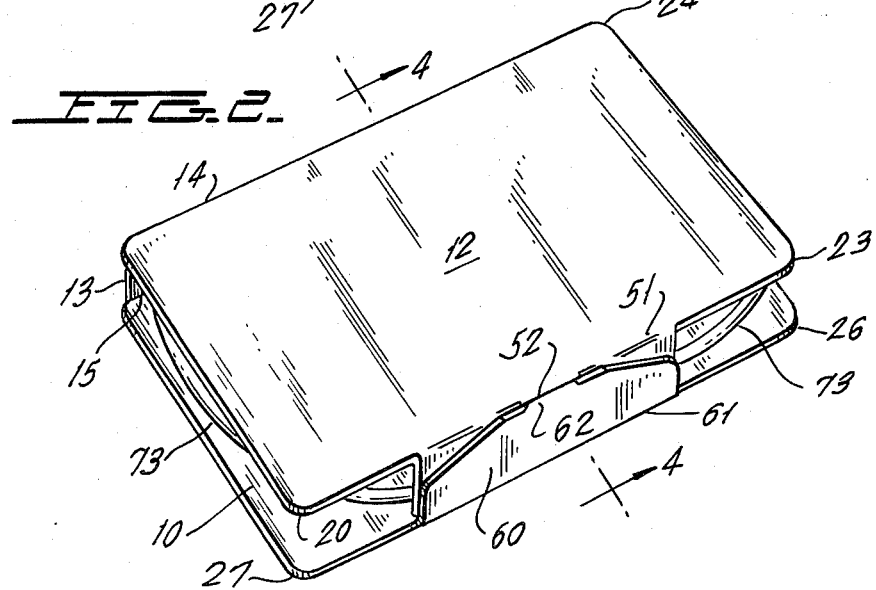
FIG. 2 is a view in perspective showing the container of FIG. 1 closed.

The bottom wall 10 is provided with the extending panel 60 connected by the fold line 61 to the bottom wall panel 10 and having the locking tab 62 extending therefrom, cut at the solid line portion 63, 63 and bent along the fold line 64. When the container is folded up to the position shown in FIGS. 2 and 4, the locking extension 62 is snapped through the notched portion 52 extending from the top wall to affect the lock of the complete unit as shown in FIG. 2.

As will be seen from a comparison of FIGS. 1 and 3, the tube 70 to be packaged is wound into coil form and held securely in the notches 43, 44, 45 of the tabs 35, 36, 37. The fitting 71 which can consist of any desired structural member connected to the tube end 70 is shown here as having a rigid tube 72 connected to the section 73 of the tube 70. The rigid tube 72 is held by the two tabs 35, 36. Should the fitting 71 be omitted, the tube 70 may be extended through the tabs 35 and 36. It should be noted here that the fitting 71 is itself essentially tubular including the rigid tubular member 72 so that it may be supported by the tabs 35, 36. The tab 37 is shown here as supporting an end 76 of the tube 70 which in turn is connected to another fitting 77 which may extend substantially diametrically of the coil formed by the tube 70 which is held by reason of the tabs 35, 36, 37.

Here the tube 70 is shown with fittings at each end. Where the fittings are omitted, should that be required for any purpose, one end of the tube will pass through the tabs 35, 36 and the other end of the tube after having been coiled within the container will pass through the tab 37.

In the case shown the fitting 71 is so arranged that it is essentially tubular and since it is connected to the end 73 of the tube 70, it constitutes essentially an extension of the tube 70 and is supported in its tubular form by the tabs 35, 36.

The fitting 77 is supported by reason of the fact that it is connected to the end 76 of the tube 70, which end 76 is supported by the tab 37.

The structure may be regarded as a container, a folder or a wrapper. Essentially, however, the top and bottom walls act to fully enclose the structure and to provide a physical support therefor. The end wall sections 50 and 60 provide the interlocking means to secure the walls of the top and bottom walls together. The tabs 35, 36, 37 serve to mount the coiled tube and the fittings in position.

The container or folder when thus formed may be completed and turned into a sterile package by wrapping in a thermoplastic sheet which may be welded in place or otherwise sealed around the container. Sterilization at appropriate temperatures may then take place in order to ensure an aseptic environment for the material until it is used.

When the package is then opened under preferably aseptic conditions, it is necessary only to tear the external wrapping, remove it and open up the container or folder to provide simplified access to the tube and fittings therein without the necessity for excessive manipulation or utilization of additional tools which may possibly cause a septic condition to arise.

In the foregoing the present invention has been described in connection with a preferred exemplary embodiment thereof. Since many variations and modifications of the present invention will now be obvious to those skilled in the art it is preferred that the scope of this invention be determined not by the specific disclosures herein contained by only by the appended claims.

What is claimed is:

1. A folder-container for securing a sterile coiled tube having at least one fitting attached to one end thereof, said folder-container comprising:
    a substantially rectangular side wall;
    a bottom wall foldably connected to a first edge of said side wall and disposed perpendicular to said side wall;
    a top wall foldably connected to a second edge of said side wall, said second edge of said side wall being opposite said first edge thereof, said top wall being perpendicular to said side wall and parallel to and in register with said bottom wall;
    at least two fitting holding tabs foldably connected to said bottom wall and located equidistant from said side wall, the plane of each said fitting holding tab being perpendicular to both said bottom wall and said side wall, each said fitting holding tab having a notch formed in the end thereof opposite said bottom wall for securing said fitting; and
    at least one tube holding tab foldably connected to and perpendicular to said bottom wall, each said tube holding tab having a notch formed in the end thereof opposite said bottom wall for holding said tube, each said tube holding tab being substantially aligned with a radius of curvature of said coil whereby insertion of said fitting in said fitting holding tabs and insertion of said tube in said tube holding tab retains said coiled tube in a coiled arrangement within said folder-container.

2. The folder container of claim 1, wherein said at least two fitting holding tabs and said at least one tube holding tab are excised on all sides, except the foldable connection thereof with the bottom wall, from the material of the bottom wall and are foldable out of the plane of the bottom wall to a position perpendicular thereto to receive said tube and said fitting.

3. The folder-container of claim 2, wherein the end of the top wall opposite the connection thereof to the side wall is provided with an extension foldably connected thereto and rotatable to a position parallel to said side wall; an opening at the fold between said extension and said top wall; the opposite end of the bottom wall having an extension foldably connected thereto extending in a direction away from the connection of said bottom wall with said side wall and being foldable into a position parallel to the first mentioned extension of said top wall; the outer end of said bottom wall also having an additional tab insertable into the said notch at the fold line between said extension and said top wall.

4. The folder-container of claim 3, wherein a flexible tearable wrapper encases the entire folder-container and contents.

* * * * *